June 3, 1975 R. KORDES Plant Pat. 3,724
ROSE PLANT
Filed Feb. 11, 1974
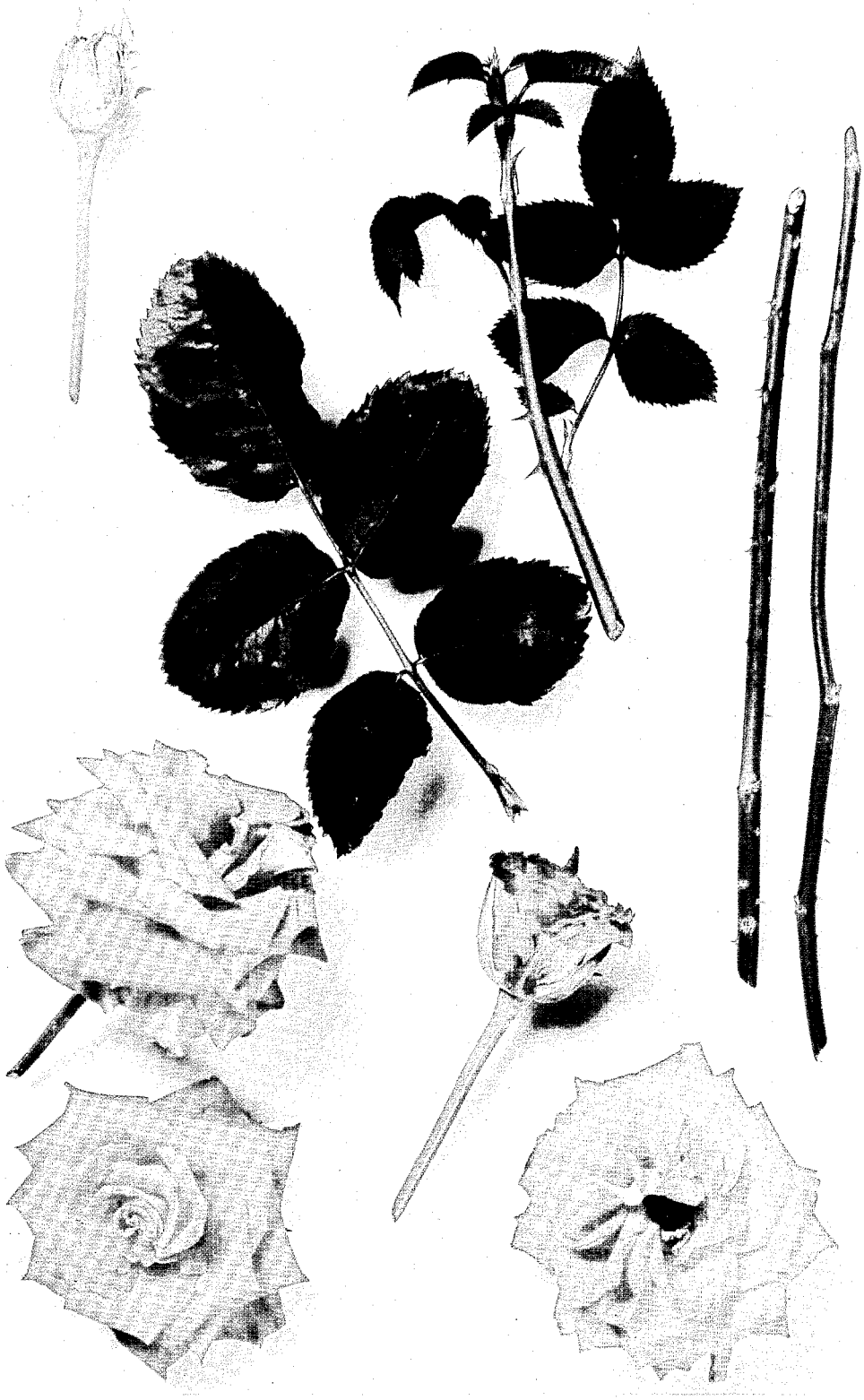

United States Patent

Plant Pat. 3,724

Patented June 3, 1975

3,724

ROSE PLANT

Reimer Kordes, Sparrieshoop, Germany, assignor to Jackson & Perkins Company, Medford, Oreg.

Filed Feb. 11, 1974, Ser. No. 441,381

Int. Cl. A01h *5/00*

U.S. Cl. Plt.—28 1 Claim

This invention relates to a new and distinct cultivar of rose plant of the floribunda class originated by me by crossing the variety Anabell (not patented in U.S.) with pollen from a seedling cultivar.

The primary objective of this breeding was to produce a new and improved cultivar of the floribunda class bearing brightly colored, long lasting flowers especially suitable as a cut flower cultivar.

This objective was fully achieved along with other desirable improvements as evidenced by the following unique combination of characteristics which are outstanding in the cultivar and which distinguish it from its parents as well as from all other cultivars of which I am aware:

1. A bushy, compact plant habit when grown outside and a well branched heavy producing plant when grown in a greenhouse.
2. Stiff and erect stems.
3. Stiffness of petals and shape of petals giving a high-centered flower form which keeps very well as a cut flower.
4. An exceptionally clear, bright color very near to Munsells Yellowish Red 7.5 R 5/12.
5. Little fragrance.

Asexual reproduction of this new cultivar by budding as performed at Elmshorn, Holstein, Germany, and Wasco, Calif., shows that the aforementioned characteristics come true to form, and are established and transmitted through succeeding propagations.

The accompanying illustration shows typical specimens of the vegetative growth and flowers of this new cultivar in different stages of development and as depicted in color as nearly true as it is reasonably possible to make the same in a color illustration of this character.

The following is a detailed description of my new rose cultivar, with color terminology in accordance with Munsells Book of Color, except where ordinary dictionary meanings are applied.

Parentage: Seedling.
- *Seed parent.*—Anabell.
- *Pollen parent.*—Seedling.

Classification:
- *Botanic.*—Rosa hybrid.
- *Commercial.*—Floribunda.

FLOWER

Observations were made at Irvine, Calif., early October.

Blooming habit: Recurrent—continuous.

Bud:
- *Size.*—¾" to 1" when petals start to unfurl.
- *Form.*—Blunt top, ovoid.
- *Color.*—When sepals first divide—Near Yellowish Red 7.5 R 4/10. When half blown; upper side of petals—Near Yellowish Red 7.5 R 5/12; lower side of petals—same.
- *Sepals.*—Color: Outer surface—Near Green Yellow 5.0 GY 8/6. Inner surface—similar color to outside but moderately covered with white tomentum. Three appendaged sepals normally appendaged. Two unappendaged sepals hairy edged.
- *Receptacle.*—Color: Near Green-Yellow 5.0 GY 8/6. Shape: Tapered. Size: Small. Surface: Smooth.

- *Peduncle.*—Length: Short. Surface: Sparsely prickly. Color: Near Green-Yellow 5.0 GY 8/6. Strength: Stiff, erect.

Bloom:
- *Size.*—Medium. Average size when fully expanded, 2½" to 3".
- *Borne.*—Singly and several together.
- *Stems.*—Medium, strong.
- *Form.*—When first open, high centered. Permanence—outer petal edges slightly curled.
- *Petalage.*—Number of petals under normal conditions, 25 to 30.
- *Color.*—Center of flower: Upper side of petals—Near Yellowish Red 7.5 R 5/12. Reverse side of petals—slightly lighter than upper side—Near Yellowish Red. 7.5 R 6/12. Outer petals: Upper side of petals—same; Reverse of petals—same. Base of petals—small area near Yellow 5.0 Y 8/14 or lighter. General tonality from a distance—Yellowish Red 7.5 R 5/12. Variegations: Occasionally a greenish streak in outer petal.
- *Discoloration.*—General tonality at end of first day—no change. Third day—no change.
- *Fragrance.*—Slight.
- *Petals.*—Thick.
- *Surface.*—Inside—satiny. Reverse—shiny.
- *Shape.*—Round.
- *Form.*—Tips slightly recurved. Petals are shaped so as to give a high centered flower form.
- *Arrangement.*—Imbricated.
- *Petaloids in center.*—Few.
- *Persistence.*—Drop off cleanly.
- *Lastingness.*—On the plant—very long; as a cut flower—very long.

Reproductive parts:
- *Stamens, Anthers.*—Medium. Color—yellow. Arrangement—regular round styles.
- *Stamens, filaments (threads).*—Medium. Color—yellow.
- *Pollen.*—Lemon yellow.
- *Styles.*—Loosely separated.
- *Stigmas.*—Color—yellow.
- *Ovaries.*—All enclosed in calyx.

Fruit: (Not observed.)

PLANT

Form: Bush.

Growth: Vigorous, upright, compact.

Foliage: Number of leaflets on normal mid-stem leaves, 5, occasionally 7.
- *Size.*—Large.
- *Quantity.*—Normal.
- *Color.*—New foliage: Near Yellowish Red 7.5 R 3/6. Old foliage: Greenish Green-Yellow 7.5 GY 4/6.

Leaflets:
- *Shape.*—Oval.
- *Texture.*—Upper side—leathery. Under side—smooth. Ribs and veins—ordinary.
- *Edge.*—Serrated.
- *Serration.*—Single.
- *Petiole (rachis).*—Color—green, partly reddish—upper side. Underside—prickles.
- *Stipules.*—Short, bearded.
- *Disease resistance.*—Normal resistance to mildew, under normal growing conditions at Irvine, Calif.

Wood:
- *New Wood.*—Color—reddish. Bark—smooth.
- *Old Wood.*—Color—green. Bark—smooth.

Prickles:
- *Quantity.*—On main stalks from base—ordinary. On laterals from stalk—few.
- *Form.*—Narrow base. Long, straight.

*Color when young.*—Red.
*Position.*—Irregular.

Small prickles:

*Quantity.*—On main stalks—few. On laterals—few.
*Color.*—Brown.

I claim:

1. A new and distinct cultivar of rose plant of the floribunda class, substantially as herein shown and described, characterized particularly as to novelty by the unique combination of a bushy, compact plant, high production of cut flowers in the greenhouse, large oval leaflets, and a clear, bright flower color of Yellowish-Red 7.5 R 5/12.

No references cited.

ROBERT E. BAGWILL, Primary Examiner